United States Patent
Gopinathan et al.

(10) Patent No.: US 6,248,064 B1
(45) Date of Patent: Jun. 19, 2001

(54) TELE-DIAGNOSTIC DEVICE

(75) Inventors: Govindan Gopinathan, Oradell, NJ (US); Arthur R. Tilford, Yorba Linda, CA (US)

(73) Assignee: ineedmd.com,inc., Great Neck, NY (US)

(*) Notice: Subject to any disclaimer, the term of this patent is extended or adjusted under 35 U.S.C. 154(b) by 0 days.

(21) Appl. No.: 09/188,971

(22) Filed: Nov. 10, 1998

Related U.S. Application Data

(63) Continuation-in-part of application No. 09/084,647, filed on May 26, 1998.

(51) Int. Cl.$^7$ ........................................... A61B 5/00
(52) U.S. Cl. ........................ 600/300; 600/301; 128/903
(58) Field of Search ................... 600/300–301; 128/903–4

(56) References Cited

U.S. PATENT DOCUMENTS

| | | |
|---|---|---|
| 3,888,240 | 6/1975 | Reinhold, Jr. et al. . |
| 4,016,868 | 4/1977 | Allison . |
| 4,230,127 | 10/1980 | Larson . |
| 4,381,012 | 4/1983 | Russek . |
| 4,510,939 | 4/1985 | Brenman et al. . |
| 4,583,547 | 4/1986 | Granek et al. . |
| 4,608,987 | 9/1986 | Mills . |
| 4,662,378 | 5/1987 | Thomis . |
| 4,698,848 | 10/1987 | Buckley . |
| 4,709,704 | 12/1987 | Lukasiewicz . |
| 4,979,607 | * 12/1990 | Miwa ................................. 128/904 |
| 5,007,427 | 4/1991 | Suzuki et al. . |
| 5,224,479 | 7/1993 | Sekine . |
| 5,353,793 | 10/1994 | Bornn . |
| 5,465,727 | 11/1995 | Reinhold, Jr. . |
| 5,511,546 | 4/1996 | Hon . |
| 5,640,953 | * 6/1997 | Bishop et al. ....................... 600/300 |
| 5,687,738 | * 11/1997 | Shapiro et al. ..................... 600/529 |
| 5,771,001 | * 6/1998 | Cobb .................................. 128/903 |
| 5,855,550 | * 1/1999 | Lai et al. ............................ 600/300 |

\* cited by examiner

Primary Examiner—Robert L. Nasser
(74) Attorney, Agent, or Firm—Brooks & Kushman P.C.

(57) ABSTRACT

A system (10) for collecting a plurality of diagnostic information and transmitting the diagnostic information to a remote location (18, 20, and 22a–22e) and for providing emergency treatment. The system (10) comprises, a first member (12a) adaptable to be worn on a person's first hand and a second member (12b) adaptable to be worn on a person's second hand. The members (12a and 12b) comprise a plurality of diagnostic devices and a defibrillator device. A transmitting unit for transmitting information to, and receiving information from, a remote location is provided.

100 Claims, 6 Drawing Sheets

TELE-DIAGNOSTIC DEVICE

This application is a continuation-in-part of U.S. patent application Ser. No. 09/084,647, filed May 26, 1998, entitled Emergency Medical Monitoring Device, which is hereby incorporated by reference.

TECHNICAL FIELD

This invention relates to a system, and a device for use with the system, for obtaining a plurality of medical diagnostic information and for providing emergency treatment. In particular, the present invention relates to a system, and device for use with the system, for gathering cardiac-related diagnostic information and transmitting the information from a first, remote, location, to a second location, such as a medical monitoring command center, for providing medical management information from the first location to the second location, and for providing emergency treatment to the patient at the first location.

BACKGROUND

In a hospital setting, when a situation arises, where a person in distress (i.e., a "patient") requires emergency treatment (i.e., and "emergency"), the doctor attending the patient must first evaluate the patient and determine the cause of the emergency. To do so, the doctor typically examines the patient in a methodical manner: (i) observing the patient's appearance and actions, (ii) if the situation permits, asking the patient and/or others around the patient questions, to obtain an accurate history of the illness, and (iii) performing a number of diagnostic tests such as EKG, blood pressure, pulse, blood gas analysis etc. After conducting the examination, the doctor is able to diagnose the patient's illness and decide upon a course of action (i.e., the treatment), to alleviate the medical emergency the patient is suffering from.

However, emergencies rarely occur in a setting where a doctor is in close physical proximity to the patient. Not uncommonly, emergencies occur at remote locations. Usually a paramedic is the first medical professional to reach the patient. In addition to transporting the patient to a hospital where the patient can be treated by a doctor, the paramedic typically uses a plurality of independent medical diagnostic probes, such as a blood pressure apparatus, stethoscope, and EKG device to perform a quick evaluation of the patient. The paramedic then conveys this information to a doctor so that the doctor can (i) provide the paramedic with treatment instructions, and (ii) prepare the emergency room for the incoming patient. This routine, while being the commonly accepted practice, is somewhat inefficient in that it is relatively time consuming to manipulate all of the different diagnostic probes attached to the patient to generate vital information and accurately read the display and convey the information to the doctor. Usually this is done over a local radio transmitting system, from an ambulance.

Other emergency situations occur where the patient is in a location which is not easily accessible except to persons already in that location. Typically, such situations occur in a plane, a boat, or other remote locations like ski resorts. Often times, constraints, such as budgetary restrictions, or easy access to the location of the emergency situation, limit availability of medical diagnostic equipment. In other circumstances, lack of sufficient population does not merit satisfactory medical diagnostic facilities. If an emergency situation occurs in a boat or plane, the vessel carrying the patient must reach a ground station so that the patient can be treated by a doctor at the base station or transported to a hospital by paramedics. In these cases, inevitably, more time passes before a doctor can evaluate the patient's medical condition and prescribe a course of action.

In most emergency situations, time is of the essence and is the key factor that determines the final outcome. As the passage of time before receiving treatment increases, the chances of successfully treating the patient decreases. Thus, it would be desirable to provide a device and system that could reduce the time element in the evaluation and treatment of the patient. Accordingly, a device and system which could reduce the time for evaluating a patient and transmitting the information gathered to a doctor would be desirable.

Also, it would be desirable to be able to provide a device and system which could be used by non-medical personnel (e.g., a flight attendant) which could enable a remotely located doctor to evaluate a patient and to provide emergency treatment without having to wait for a paramedic or caregiver to arrive.

During emergency situations, time is often expended adjusting the placement of EKG electrodes to take accurate EKG readings. Moreover, even in a non-emergency situation, it is often time consuming to correctly locate the proper placement of EKG electrodes. It would be desirable to provide a device which could be placed directly on the patient's chest and which could expedite the recording of accurate EKG tracings. It would also be desirable to provide a device which is capable of readily obtaining from the patient a plurality of diagnostic information and transmitting them in the shortest amount of time to help facilitate a doctor located far away from the patient to analyze the data and diagnose the emergency condition.

Accordingly, it would be desirable to provide an inexpensive and easy to use device which could (i) quickly and easily gather and transmit from a remote location a plurality of diagnostic information, which includes EKG, Blood Pressure, Pulse, temperature $\%O_2$ saturation, and heart sound monitoring, (ii) provide the ability to allow oral communication with a remote location from a medical command center, (iii) provide emergency initial treatment, and (iv) expedite the eventual transfer of the patient to the nearest medical center.

It would also be desirable to provide a device and a system which could convey all the diagnostic information mentioned above, and have the capability to recognize life threatening heart irregularities and have the ability to instantaneously defibrillate a patient.

DISCLOSURE OF THE INVENTION

An object of the present invention is to provide an inexpensive and easy to use system for gathering and transmitting a plurality of diagnostic information to a remote location.

Another object is to provide an inexpensive and easy to use system for providing emergency medical treatment at a remote location.

Yet another object of the present invention is to provide an inexpensive and easy to use probe which could gather and transmit a plurality of diagnostic information to a remote location.

Yet still another object is to provide an inexpensive and easy to use device which could provide emergency medical treatment (e.g. defibrillation) at a remote location.

In carrying out the above and other objects, a system for collecting a plurality of diagnostic information and transmitting the diagnostic information to a remote location and for providing emergency treatment is provided. The system comprises a first member adaptable to be worn on a first hand of a person, a second member adaptable to be worn on a second hand of a person, and a means for transmitting information to, and receiving information from, a remote location. Each member comprises a glove member having a palm portion, a wrist portion and five phalange portions. The members further comprise an EKG diagnostic device, a blood pressure and pulse rate device, a temperature device and a defibrillator device. Also, the members could have a $\%O_2$ device, as well as an auscultation device.

BEST MODE FOR CARRYING OUT THE INVENTION

The present invention relates to a system, and a device for use with the system, for obtaining a plurality of medical diagnostic information from, and for providing emergency treatment at, a remote location. In particular, the present invention relates to a system, and diagnostic probe and emergency treatment members and an information transmission device for use with the system, for gathering cardiac related diagnostic information and transmitting the information from a remote location to another location, such as a medical monitoring command center, and for providing emergency treatment at the remote location.

Figure 1:
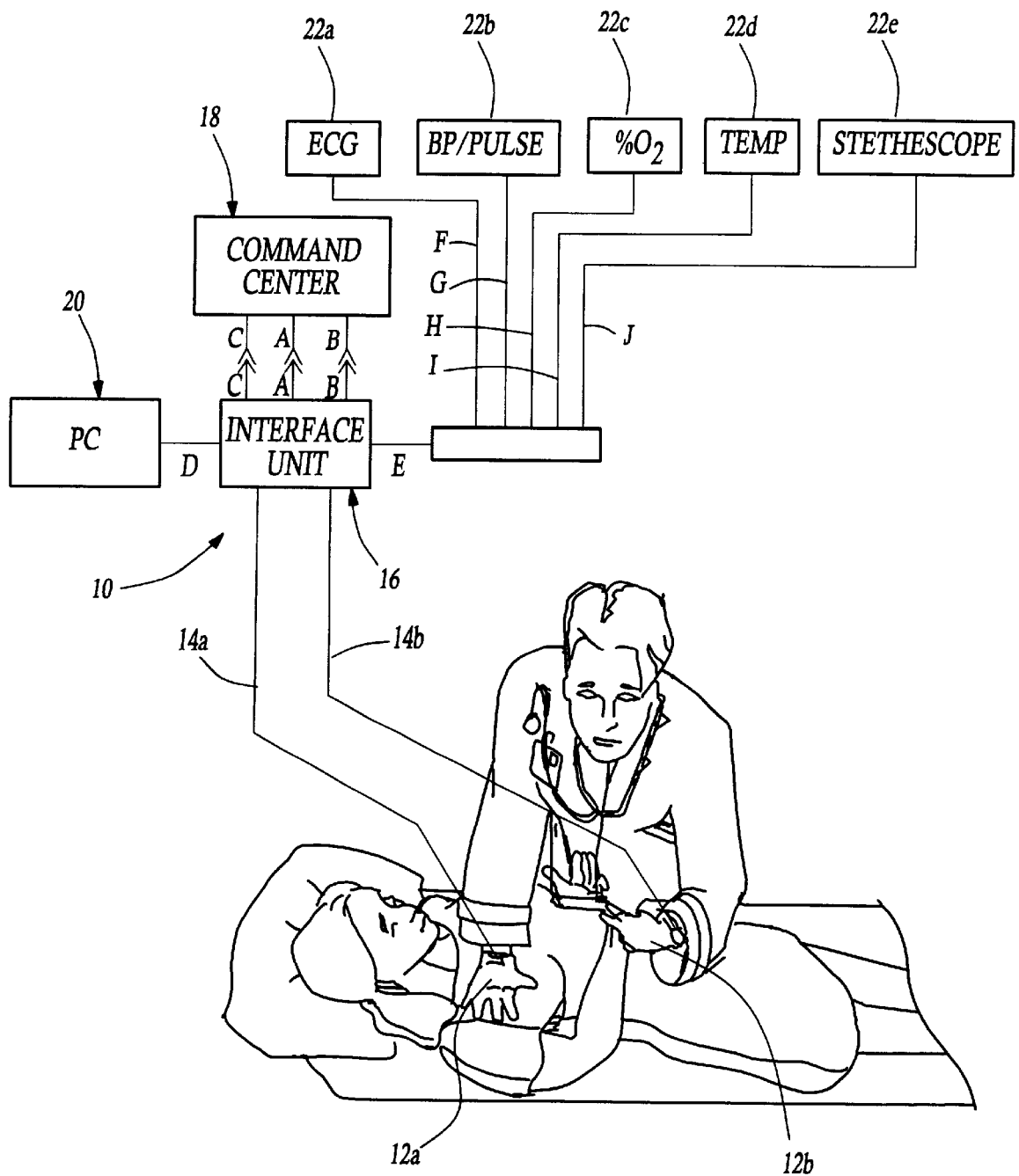
FIG. 1 is a schematic view of the system of the present invention.

As representative of the present invention, FIG. 1, illustrates a system 10 for gathering, and transmitting, from a remote location, a plurality of diagnostic information and for providing emergency treatment at the remote location. The system 10 includes a first glove member 12a and a second glove member 12b.

The first glove member 12a is adaptable to be worn over one of a person's hand. The second glove member 12b is adaptable to be worn over the other one of a person's hand. The glove members 12a and 12b include a plurality of medical diagnostic probes, which gather diagnostic signals, and emergency treatment devices, which provide emergency cardiac treatment, as will be explained in more detail below.

The glove members 12a and 12b are connected via a first cable 14a and a second cable 14b, respectively, to an interface unit 16 and, thus communicates with, and are capable of transmitting diagnostic signals, or information, from the medical diagnostic probes to the interface unit. In a preferred embodiment, the interface unit 16 communicates with a remote command center 18 via a telephone wire or fiber A, a satellite connection B, or a radio wave connection C. The interface unit 16 can alternatively communicate with a personal computer (PC) 20 via an interface connection D.

The PC 20 can be local or remote relative to the interface unit 16. The interface unit 16 may also communicate with a plurality of local or remote diagnostic readout apparatuses 22a, 22b, 22c, 22d, and 22e via a central interface connection E via a plurality of individual interface connections, F, G, H, I, and J, respectively. The diagnostic readout apparatuses 22a–e are preferably an electrocardiogram (EKG) readout; a blood pressure (BP) and pulse readout, a $\%O_2$ oxygen readout, a temperature readout, and a stethoscope, respectively.

Figure 2:
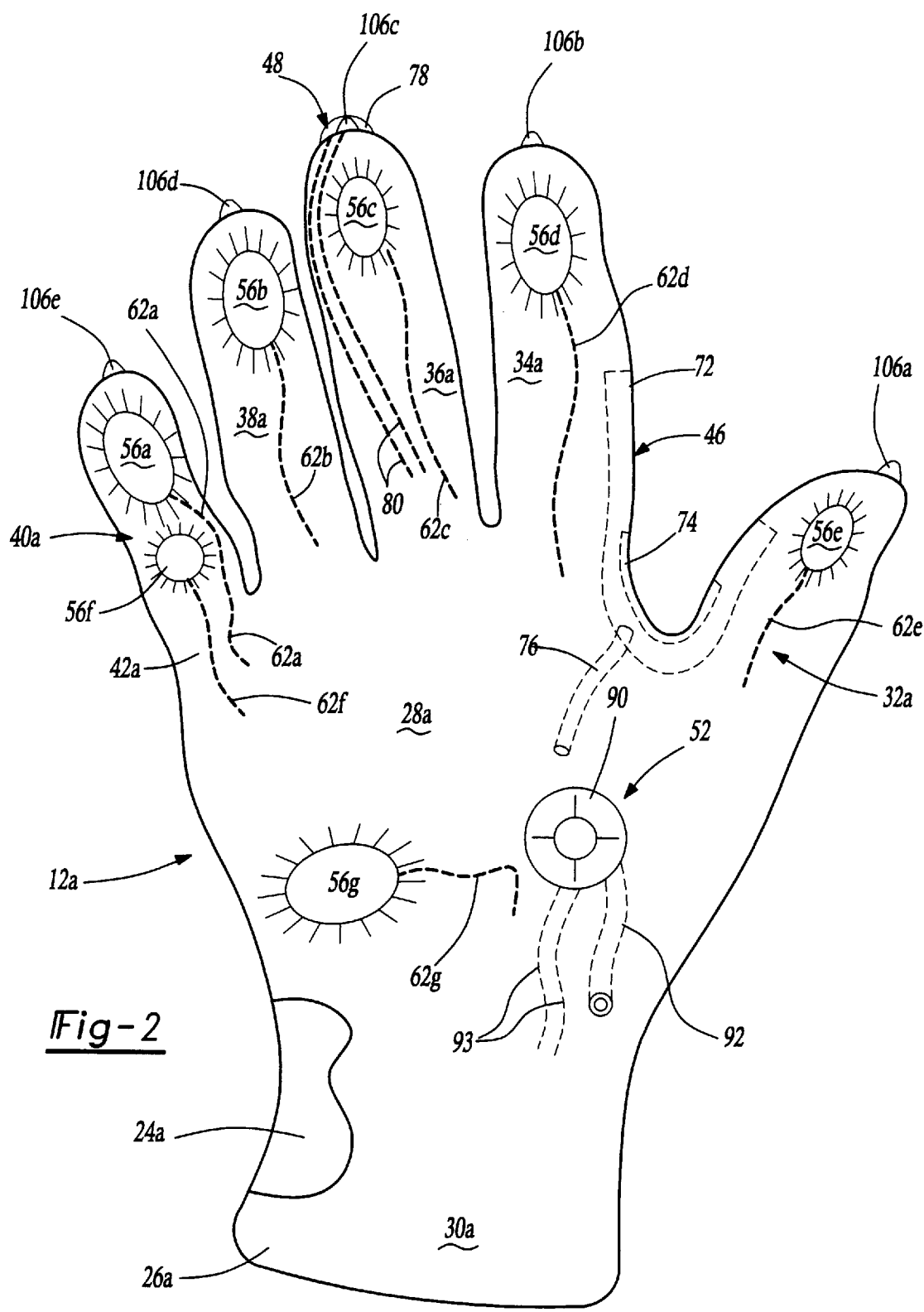
FIG. 2 is a plan view of a first side of a first apparatus of the present invention.
Figure 4:
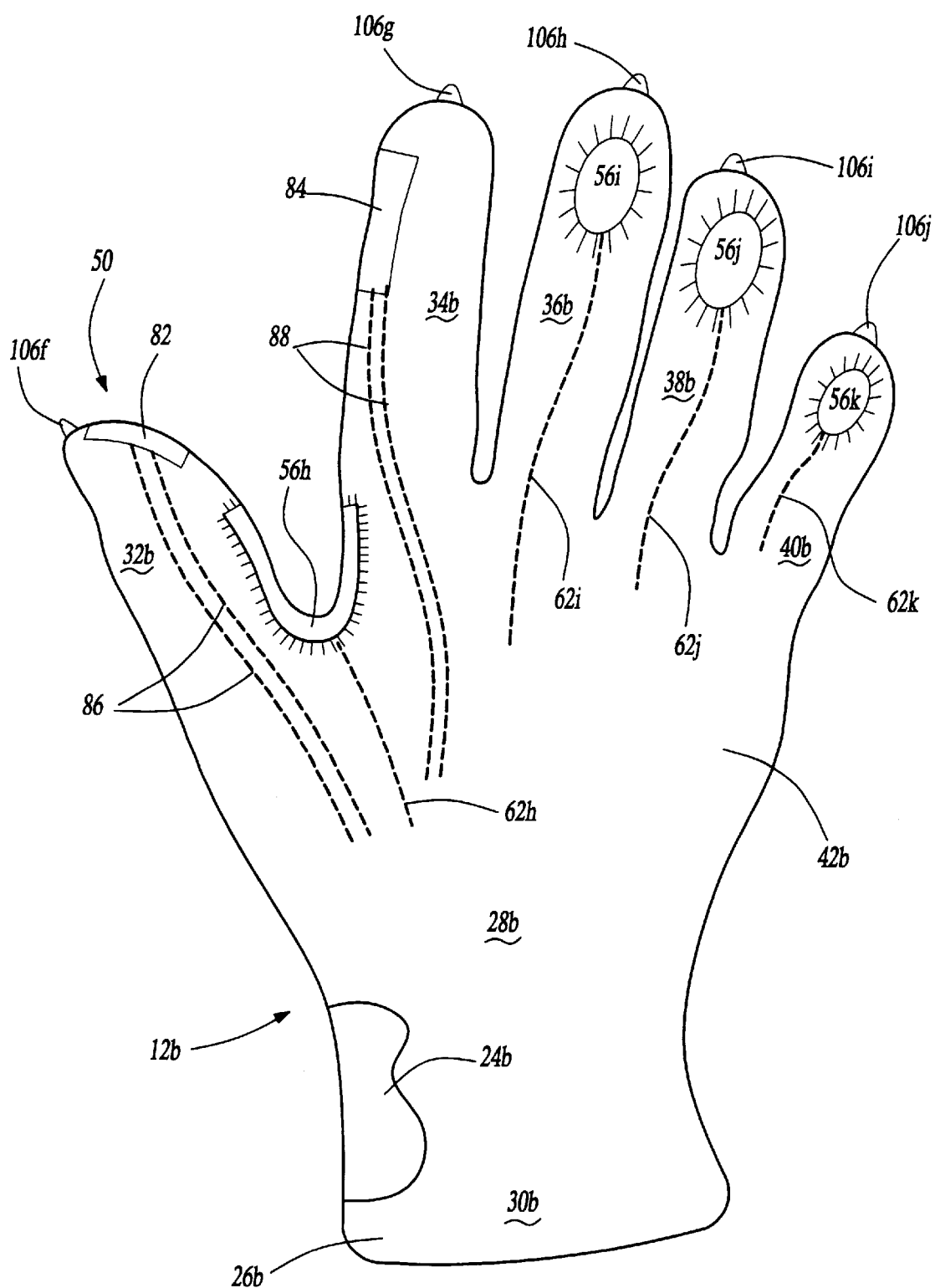
FIG. 4 is a plan view of a first side of a second apparatus of the present invention.

Referring to FIGS. 2 and 4, both the first glove member 12a and the second glove member 12b comprise a first glove layer 24a and 24b, respectfully, and a second glove layer 26a and 26b, respectively, secured to the first glove layer such that the second glove layer overlies a majority, and preferably almost all, of the first glove layer. Each of the first glove layers 24a and 24b is preferably made of a highly flexible natural or synthetic material, such as cotton flocked nitrile. Each of the second glove layers 26a and 26b is preferably made of a highly flexible material, such as nitrile.

Figure 3:
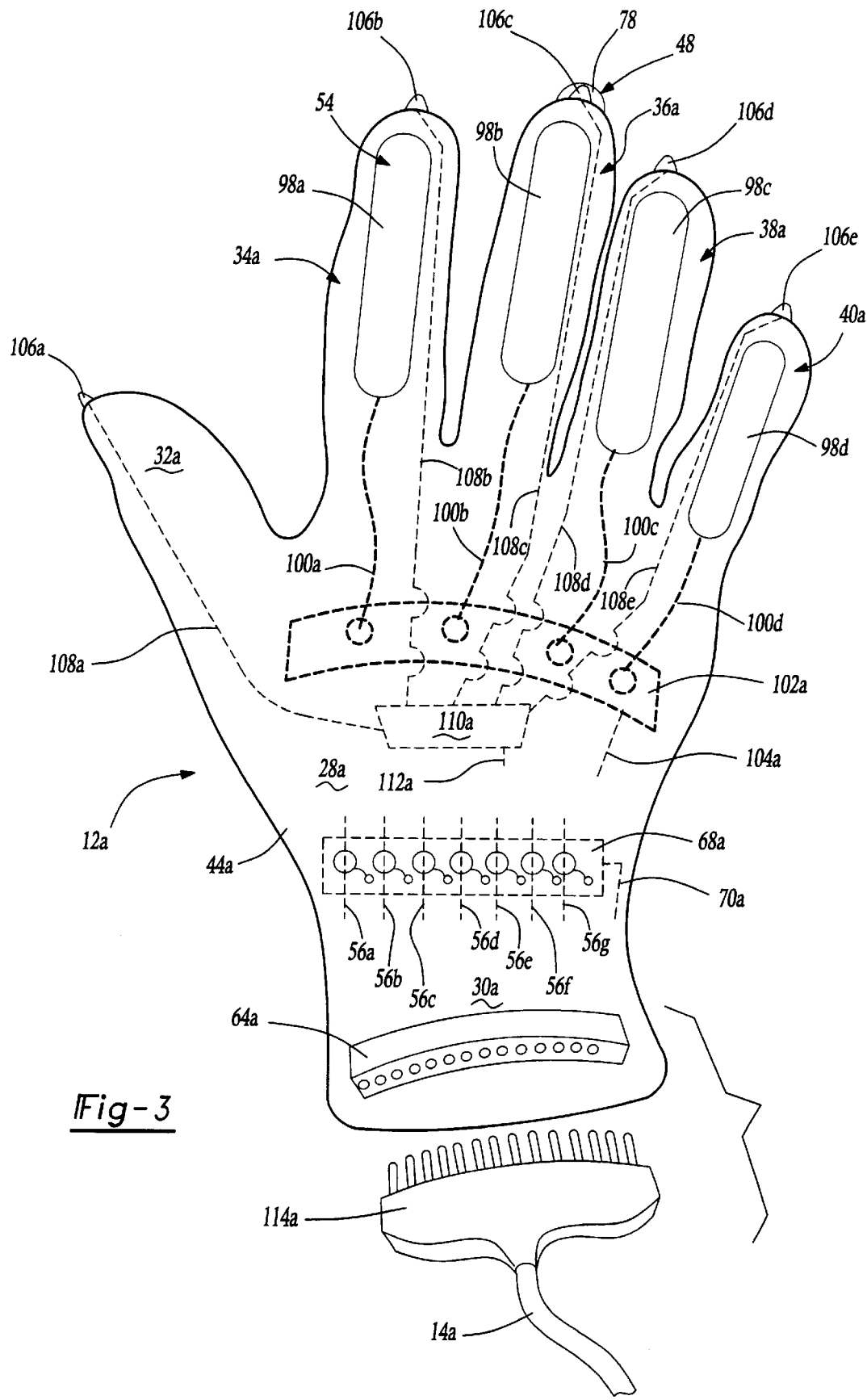
FIG. 3 is a plan view of a second side of the first apparatus of the present invention.

Referring to FIG. 2, the first glove member 12a includes a palm portion 28a, a wrist portion 30a, a thumb phalange portion 32a, an index finger phalange portion 34a, a middle finger phalange portion 36a, a ring finger phalange portion 38a, and a pinky finger phalange portion 40a. The first glove member 12a further includes a palmar surface 42a (FIG. 2) and a dorsal surface 44a (FIG. 3).

Figure 5:
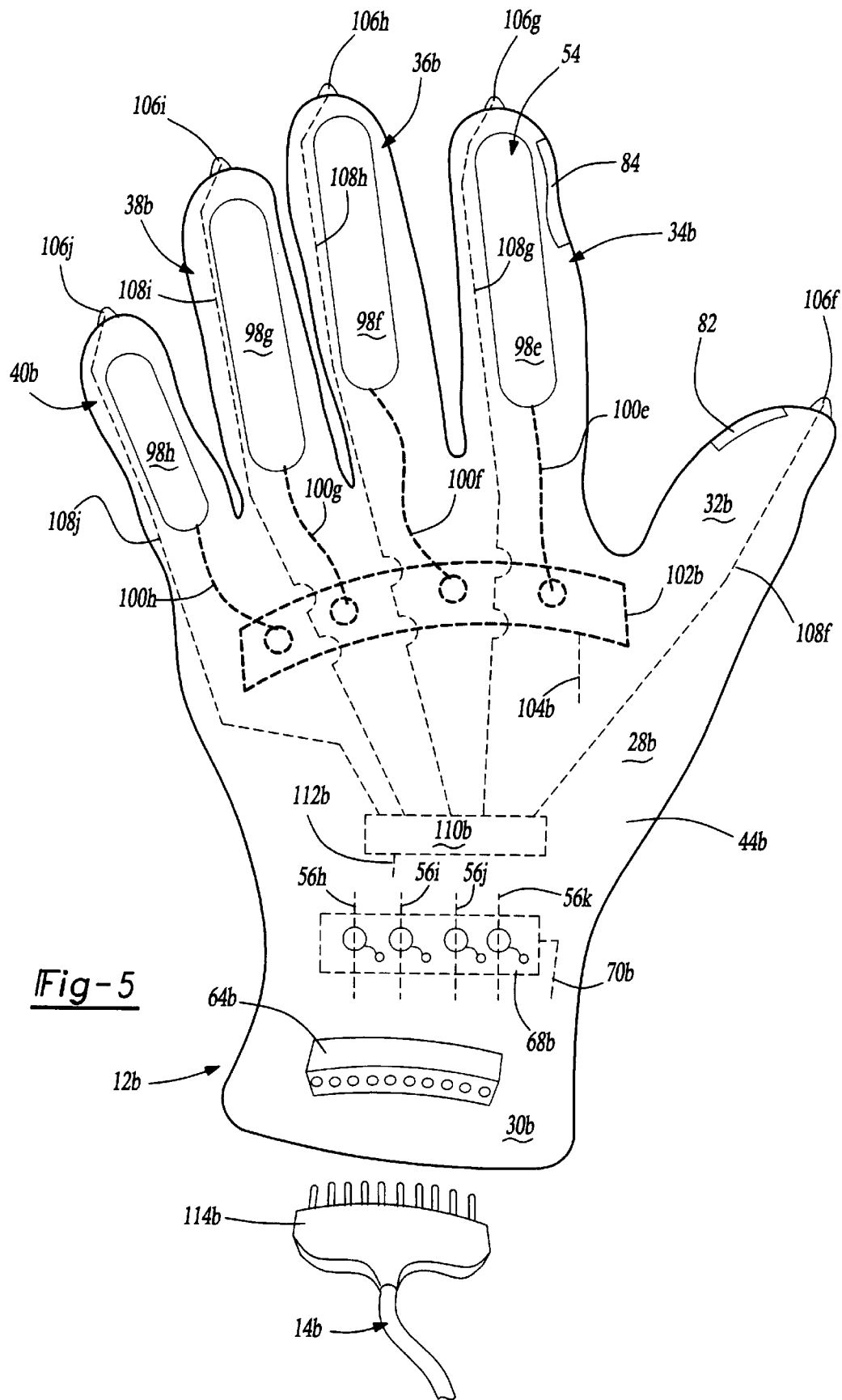
FIG. 5 is a plan view of a second side of the second apparatus of the present invention.

Referring to FIG. 4, the second glove member 12b includes a palm portion 28b, a wrist portion 30b, a thumb phalange portion 32b, an index finger phalange portion 34b, a middle finger phalange portion 36b, a ring finger phalange portion 38b, and a pinky finger phalange portion 40b. The second glove member 12b further includes a palmer side 42b and a dorsal side 44b (FIG. 5).

As discussed previously, the glove members 12a and 12b contain a plurality of medical diagnostic devices and emergency treatment devices. In the embodiments shown in FIGS. 2–5, the glove members 12a and 12b contain an EKG diagnostic device, a blood pressure and pulse rate device 46 (FIG. 2), a temperature device 48, a $\%O_2$ device 50 (FIG. 4), an auscultation device 52 (FIG. 2) and a defibrillator device 54 (FIGS. 3 and 5).

Figure 7:
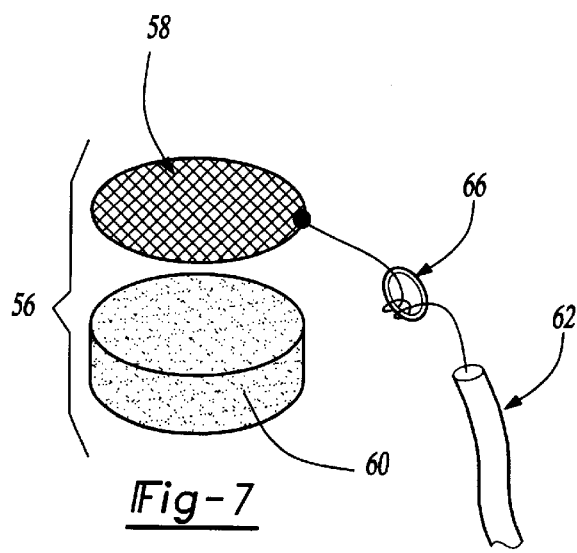
FIG. 7 is an exploded view of an EKG sensor used in FIGS. 2–5.

The EKG device is capable of measuring the EKG currents of the heart muscle and preferably includes a plurality of sensors 56a–56k located on the glove members 12a and 12b. Specifically, sensors 56a (FIG. 2), 56b, 56c, 56d, 56e 56f, 56g are located on the first glove member 12a. Sensors 56h (FIG. 4), 56i, 56j, and 56k are located on the second glove member 12b. Sensors 56a–56g (FIG. 2) are secured to the first layer 24a of the first glove member 12a. Sensors 56h–56k (FIG. 4) are secured to the first layer 24b of the second glove member 12b. An exemplary sensor 56c is shown in FIG. 7. Each of the sensors 56a–56k preferably includes a stainless-steel screen 58 and an EKG jelly sponge 60, capable of supplying EKG conductive jelly, disposed between the screen and, preferably, the respective first layer 24a and 24b (FIGS. 2 and 4). Each sensor 56a–56k is provided on the palmer surface 42a and 42b, respectively, of one of the glove members 12a and 12b and, preferably, extends through each respective glove member so that the sensor is exposed to the environment.

More specifically, sensor 56a (FIG. 2) is positioned on the tip portion of the palmar surface 42a of the pinky finger phalange portion 40a of the first glove member 12a. Sensor 56b is positioned on the tip portion of the palmer surface 42a of the ring finger phalange portion 38a of the first glove member 12a. Sensor 56c is positioned on the tip portion of the palmer surface 42a of the middle finger phalange portion 36a of the first glove member 12a. Sensor 56d is positioned on the tip portion of the palmer surface 42a of the index finger phalange portion 34a of the first glove member 12a. Sensor 56e is positioned on the tip portion of the palmar surface 42a of the thumb phalange portion 32a of the first glove member 12a. Sensor 56f is positioned on the base portion of the palmar surface 42a of the pinky finger phalange portion 40a of the first glove member 12a. Sensor 56g is positioned on the left side, as viewed in FIG. 2, of the palmar surface 42a of the palm portion 28a of the first glove member 12a.

Sensor 56h (FIG. 4) is positioned on the palmer surface 42b and the dorsal surface 44b (FIG. 5) of the thumb phalange portion 32b and the index finger phalange portion 34b of the second glove member 12b. The sensor 56h extends from the base portion of the thumb phalange portion 32b of the second glove member 12b to the base portion of the index finger phalange portion 34b of the second glove member. Sensor 56i is positioned on the tip portion of the palmer surface 42b of the middle finger phalange portion 36b of the second glove member 12b. Sensor 56j is positioned on the tip portion of the palmer surface 42b of the ring finger phalange portion 38b of the second glove member 12b. Sensor 56k is positioned on the tip portion of the palmer surface 42b of the pinky finger phalange portion 40b of the second glove member 12b.

Each of the sensors 56a–56g (FIG. 2) is connected to a wire 62a–62g, respectively, which extends between and electrically connects a respective one of the sensors 56a–56g with a first female connection plug 64a (FIG. 3), which is preferably provided on the dorsal surface 44a of the first glove member 12a. Each wire 62a–62g is preferably disposed between the first and second layers 24a and 26a of the first glove member 12a, and is preferably secured to the first layer 24a. Each of the sensors 56h–56k (FIG. 4) is connected to a wire 62h–62k, respectively, which extends between and electrically connects a respective one of the sensors 56h–56k with a second female connection plug 64b (FIG. 5), which is preferably provided on the dorsal surface 44b of the second glove member 12b. Each wire 62h–62k is preferably disposed between the first and second layers 24b and 26b of the second glove member 12b, and is preferably secured to the first layer 30b. Each wire 62a–62k is preferably a highly flexible stranded No. 30 (or smaller) wire which is shielded and has a powdered-iron bead 66 (FIG. 7), such as Part No. T25-26 from Amidon Associates in Santa Ana, Calif., disposed adjacent to its respective sensors 56a–56k to help prevent the detection of unwanted noise.

The first glove member 12a includes a first ground strip 68a (FIG. 3) which is preferably positioned on the dorsal surface 44a of the palm portion 28a between the first and second layers 24a and 26a, respectively. Each wire 62a–62g is connected to the first ground strip 68a, preferably, via each respective wire's shield. The first ground strip 68a is connected to a wire 70a, which extends between and electrically connects the first ground strip 68a to the first female connection plug 64a. The second glove member 12b includes a second ground strip 68b (FIG. 5) which is preferably positioned on the dorsal surface 44b of the palm portion 28b between the first and second layers 24b and 26b, respectively. Each wire 62i–62k is connected to the second ground strip 68b, preferably, via each respective wire's shield. The second ground strip 68b is connected to a wire 70b, which extends between and electrically connects the second ground strip 68b to the second female connection plug 64a. The first and second ground strips 68a and 68b, respectively, are composed of highly flexible copper mesh or foil and function to bring existing electromagnetic forces (EMF) noise to a single electrical voltage point for removal.

The blood pressure device 46 (FIG. 2), which is capable of measuring systolic and diastolic blood pressure and pulse rate signals, is preferably secured to the first layer 24a of the first glove member 12a between the first layer 24a and the second layer 26a on the thumb phalange portion 32a and the index finger phalange portion 34a of the of the first glove member 12a. The blood pressure device 46 preferably includes an expandable air bladder 72 defining a chamber for accommodating air or another suitable inflation fluid, an acoustical coupler 74 in the chamber and an air tube 76. The air bladder 72 extends from the mid-portion of the thumb phalange portion 32a of the first glove member 12a to the mid-portion of the index finger phalange portion 34a. The air tube 76 extends between and provides fluid and audio communication between the chamber of the air bladder 72 and the first female connection plug 64a (FIG. 3). The acoustical coupler 74 (FIG. 2) is capable of collecting the sound waves in the air bladder 72 and directing the sound waves towards, and through, the air tube 76. The blood pressure device 46 is preferably made of parts similar, or identical, to parts of the UB-302 a Systolic/Diastolic (Pulse) Digital Blood Pressure monitor from A+D Engineering Inc., of Milpitas, Calif.

The temperature device 48 is capable of measuring temperature signals and preferably includes a thermistor 78. The thermistor 78 is preferably positioned on the tip of the middle finger phalange portion 36a of the first glove member 12a. The thermistor 78 is preferably secured to the first layer 24a of the first glove member 12a and extends through the second layer 26a. The temperature device 48 includes a pair of highly flexible No. 30 (or smaller) stranded and shielded wires 80 which extend between and electrically connect the thermistor 78 and the first female connection plug 64a (FIG. 3). The temperature device 48 (FIG. 2) is preferably made of parts similar, or identical, to parts of the Cole-Parmer E-08402-00 thermometer and Generic thermistor E-08459-10 from Cole-Parmer Instrument Company of Vernon Hills, Ill.

The %$O_2$ device 50 (FIGS. 4 and 5) is capable of measuring the percent oxygen saturation in the blood (%$O_2$) signals and preferably includes a red (600–660 nm) and infra-red (880–1000 nm) LED emitter 82 and an LED (600–1000 nm) sensor 84 positioned on the second layer 26b of the second glove member 12b. The LED emitter 82 is preferably secured to the inner side of the thumb phalange portion 32b of the second glove member 12b and the LED sensor 84 is preferably secured to the side of the index finger phalange portion 34b facing the thumb phalange portion 32b of the second glove member 12b such that the LED emitter 82 faces the LED sensor 84. The LED emitter 82 is connected to a pair of highly flexible No. 30 (or smaller) stranded and shielded wires 86 which extend between and electrically connect the LED emitter and the second female connection plug 64b (FIG. 5). The LED sensor 84 (FIG. 4) is connected to a pair of wires 88 which extend between and electrically connect the LED sensor and the second female connection plug 64b (FIG. 5). The %$O_2$ device 50 (FIGS. 4 and 5) is preferably made of parts similar, or identical, to parts of the Nonin Onyx blood flow and oxygen % reader, model No. 8500M from Nonin Medical, Inc., of Plymouth, Minn..

The auscultation device 52 (FIG. 2) is capable of detecting the sound waves local to the patient's heart and lungs and preferably includes an acoustical coupler and microphone 90, an air tube 92, and a pair of highly flexible No. 30 (or smaller) stranded and shielded wires 93. The acoustical coupler and microphone 90 is preferably secured to the right side of the palmer surface 42a of the palm portion 28a of the first glove member 12a, preferably on the first layer 24a. The acoustical coupler and microphone 90 is capable of collecting and amplifying sound waves which are in relative close proximity to the acoustical coupler and microphone. The air tube 92 extends between and provides audio communication between the acoustical coupler and microphone 90 and the first female connection plug 64a, which is adaptable for connection with a stethoscope. The air tube 92, thus when connected with a stethoscope, extends between and provides audio communication between the acoustical coupler and microphone 90 and the stethoscope. The pair of wires 93 extends between and electrically connects the acoustical coupler and microphone 90 and the first female connection plug 64a (FIG. 3). The auscultation device 52 (FIG. 2) is preferably made of parts similar, or identical, to parts of the EG Company microphone 9445 from the Electrical Gold Co. Of Scottsdale, Ariz..

The defibrillator device 54 (FIGS. 3 and 5) is capable of providing an electrical shock to restore the rhythm of a ventrically fibrillating heart. The defibrillator device 54 includes a plurality of electrodes 98a–98h located on the dorsal surfaces 44a and 44b, respectively, of the second layer 26a and 26b, respectively, of the first glove member 12a and the second glove member 12b, respectively.

More specifically, electrode 98a (FIG. 3) is positioned on the dorsal surface 44a of the index finger phalange portion 34a of the first glove member 12a. Electrode 98b is positioned on the dorsal surface 44a of the middle finger phalange portion 36a of the first glove member 12a. Electrode 98c is positioned on the dorsal surface 44a of the ring finger phalange portion 38a of the first glove member 12a. Electrode 98d is positioned on the dorsal surface 44a of the pinky finger phalange portion 40a of the first glove member 12a.

Electrode 98e (FIG. 5) is positioned on the dorsal surface 44b of the index finger phalange portion 34b of the second glove member 12b. Electrode 98f is positioned on the dorsal surface 44b of the middle finger phalange portion 36b of the second glove member 12b. Electrode 98g is positioned on the dorsal surface 44b of the ring finger phalange portion 38b of the second glove member 12b. Electrode 98h is positioned on the dorsal surface 44b of the pinky finger phalange portion 43b of the second glove member 12b.

Each of the electrodes 98a–98d (FIG. 3) is connected to a wire 100a–100d, respectively, that extends between and electrically connects a respective one of the electrodes 98a–98d with a first defibrillator electrode combiner 102a, which is preferably positioned on the dorsal surface 44a of the first glove member 12a. The first defibrillator electrode combiner 102a is connected to a highly flexible No. 24 (or smaller) stranded high voltage insulated wire 104a which extends between and electrically connects the first defibrillator electrode combiner 102a to the first female connection plug 64a.

Each of the electrodes 98e–98h (FIG. 5) is connected to a highly flexible No. 24 (or smaller) stranded high voltage insulated wire 100e–100h, respectively, that extends between and electrically connects a respective one of the electrodes 98a–98d with a second defibrillator electrode combiner 102b, which is preferably positioned on the dorsal surface 44b of the second glove member 12b. The second defibrillator electrode combiner 102b is connected to a highly flexible No. 24 (or smaller) stranded high voltage insulated wire 104b which extends between and electrically connects the second defibrillator electrode combiner 102b to the second female connection plug 64b. The defibrillator device 54 is preferably made of parts similar, or identical, to parts of the Heartstream automatic defibrillator model "E" or "EM" of the Heartstream Co., of Seattle, Wash.

The glove members 12a and 12b preferably further comprise an acupuncture device for providing a voltage of sufficient potential to create electrical pin stimulations. The acupuncture device preferably includes a plurality of stainless steel electrodes 106a–106j (FIGS. 3 and 4) positioned at the tip of, and extending away from, a respective phalange portion 32a–40a, and 32b–40b, respectively, on a respective glove member 12a and 12b. Each electrode 106a–106j is essentially conical and has a base portion connected to a respective phalange portion 32a–40a and 32b–40b, respectively, and terminates in a head portion. Each of the electrodes 106a–106e (FIG. 3) includes a wire 108a–108e, respectively, that extends between and electrically connects a first acupuncture electrode combiner 110a with a respective one of the electrodes 106a–106e. The first acupuncture electrode combiner 110a is connected to a wire 112a which extends between and electrically connects the first acupuncture electrode combiner 110a with the first female connection plug 64a. Each of the electrodes 106f–106j (FIG. 5) includes a wire 108f–108j, respectively, that extends between and electrically connects a second acupuncture electrode combiner 110b with a respective one of the electrodes 106f–106j. The second acupuncture electrode combiner 110b is connected to a wire 112b which extends between and electrically connects the second acupuncture electrode combiner 110b with the second female connection plug 64b.

Each of the glove members 12a and 12b is preferably manufactured by securing, by any suitable means, the wires, sensors, electrodes and other components to a respective glove, preferably made of nitrile (i.e., the first layers 24a and 24b). It should be noted that the wires, sensors and/or electrodes could be made using flexible circuit technology, such as by using a conductive printable ink. The components of the glove member 12a and 12b which do not extend past the second layers 26a and 26b, such as the wires, are then covered by the respective second layer 26a and 26b in a suitable manner, such as by spraying or dip coating.

Figure 6:
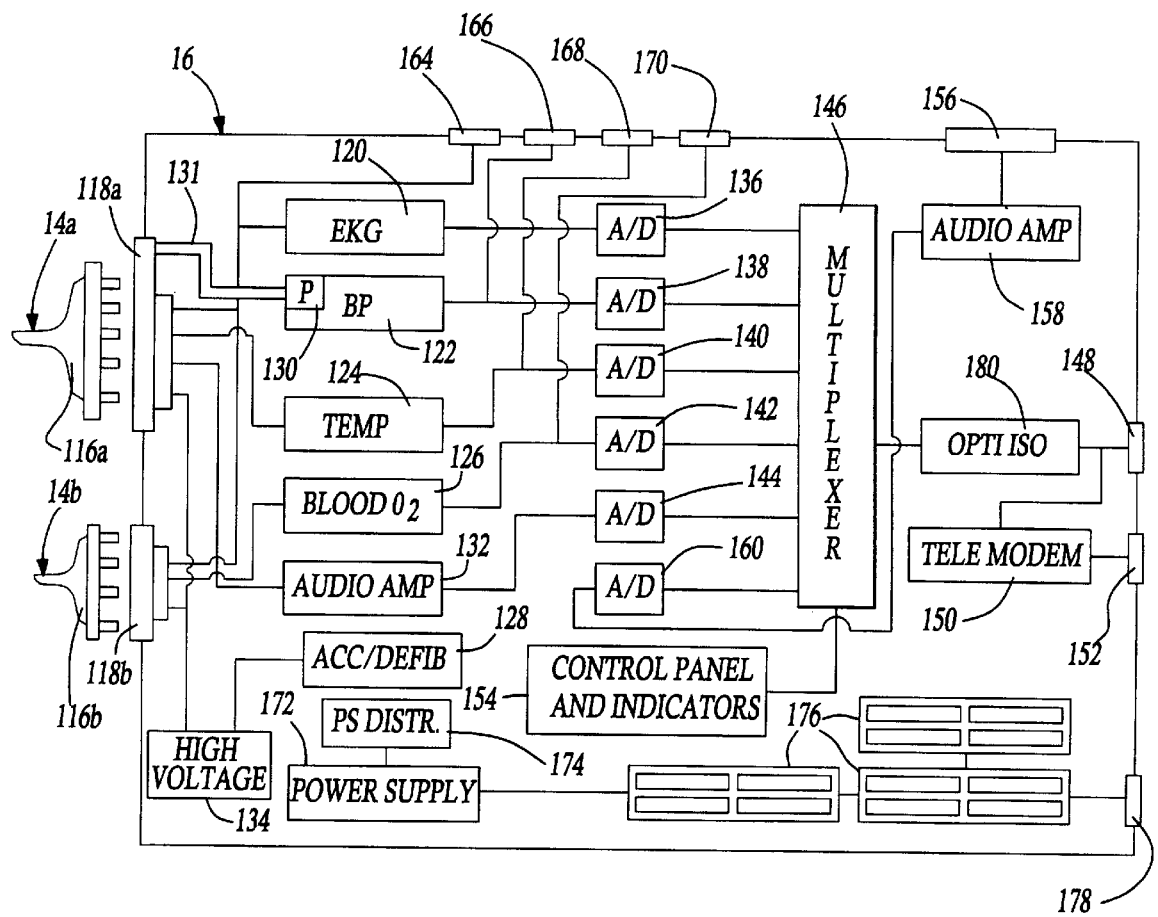
FIG. 6 is a schematic diagram of the circuit of the interface unit shown in FIG. 1.

The first cable 14a includes a first input plug 114a (FIG. 3), which plugs into male receptors on the first female connection plug 64a on the first glove member 12a, and a first output plug 116a (FIG. 6), which plugs into male receptors on a first female connection plug 118a on the interface unit 16. The second cable 14b includes a first input plug 114b (FIG. 5), which plugs into male receptors on the second female connection plug 64b on the second glove member 12b, and a second output plug 116b (FIG. 6), which plugs into male receptors on a second female connection plug 118b on the interface unit 16. The first cable 14a (FIG. 3) preferably includes a plurality of electrical wires and air tubes which extend between plugs 114a and 116a (FIG. 6) to provide electrical, audio, and fluid communication between the first glove member 12a and the interface unit 16 when the plugs 114a (FIG. 3) and 116a (FIG. 6) are plugged into their respective female connection plugs 64a (FIG. 3) and 118a (FIG. 6). The second cable 14b (FIG. 5) preferably includes a plurality of electrical wires which extend between plugs 114b and 116b (FIG. 6) to provide electrical communication between the second glove member 12b and the interface unit 16 when the plugs 114b (FIG. 5) and 116b (FIG. 6) are plugged into their respective female connection plugs 64b (FIG. 5) and 118b (FIG. 6).

The interface unit 16 (FIG. 6) preferably includes an EKG circuit board 120 for receiving EKG currents detected by the sensors 56a–56k (FIGS. 2 and 4), a blood pressure circuit board 122 (FIG. 6) for receiving systolic and diastolic blood pressure and pulse rate signals from the blood pressure device 46 (FIG. 2), a temperature circuit board 124 (FIG. 6) for receiving temperature signals from the temperature device 48 (FIG. 2), a $\%O_2$ circuit board 126 (FIG. 6) for receiving $\%O_2$ signals from the $\%O_2$ device 50 (FIG. 4) and an acupuncture/defibrillator circuit board 128 (FIG. 6) for controlling the delivery of electrical shock to the patient.

The EKG circuit board 120 is capable of amplifying the EKG currents from the sensors 56a–56k and converting the EKG currents to at least a plurality of EKG analog outputs. The EKG circuit board 120 is preferably made of parts similar, or identical, to parts of the PC-ECG recorder unit from I.P.I. Medical Products of McLean, Va.

The blood pressure circuit board 122 is capable of (i) converting the systolic blood pressure signals to a systolic blood pressure analog output, (ii) the diastolic blood pressure signals to a diastolic blood pressure analog output, and (iii) the pulse rate signals to a pulse rate analog output. The blood pressure circuit board 122 includes a source of inflation fluid, such as an air pump 130 (FIG. 6), for supplying a source of inflation fluid for the air bladder 72, and an acoustical sensor (not shown) for detecting the systolic and diastolic blood pressure and pulse rate signals. The pump 130 is in fluid communication with the air bladder 72 (FIG. 2) via the air tube 76, cable 14a (FIG. 1) and air conduit 131 (FIG. 6), which extends between and provides fluid and audio communication between the female connection plug 118a of the interface unit 16 and the air pump 130 of the blood pressure circuit board 122. The blood pressure circuit board 122 is preferably made of parts similar, or identical, to parts of the UB-302 Systolic/Diastolic (Pulse) Digital Blood Pressure monitor from A+D Engineering Inc., of Milpitas, Calif.

The temperature circuit board 124 is capable of converting the temperature signals to a temperature analog output. The temperature circuit board 124 is preferably made of parts similar, or identical, to parts of the Cole-Parmer E-08402-00 digital thermometer from Cole-Parmer, of Vernon Hills, Ill. The $\%O_2$ circuit board 126 is capable of converting the $\%O_2$ signals to a $\%O_2$ analog output. The $\%O_2$ circuit board 124 is preferably made of parts similar, or identical to parts of the Nonin Onyx blood flow and oxygen % reader, model No. 8500M from Nonin Medical, Inc., of Plymouth, Minn. The interface unit 16 also includes a first audio amp 132 for amplifying the sound waves received from the auscultation device 52 (FIG. 2). The acupuncture defibrillator circuit board 128 selectively regulates the amount of electrical energy supplied by the defibrillator device 54 (FIG. 3) and the acupuncture device. A high voltage source 134 is contained within the interface unit 16 which supplies power to the electrodes 98a–98k to generate the electrical shock to be delivered to the patient and also supplies power to electrodes 106a–106j (FIGS. 3 and 5).

The interface unit 16 further includes a first analog to digital converter 136 for converting the EKG analog outputs to an EKG digital data stream, a second analog to digital converter 138 for converting (i) the systolic blood pressure analog output to a systolic blood pressure digital data stream, (ii) the diastolic blood pressure analog output to a diastolic blood pressure digital data stream, and (iii) the pulse rate analog output to a pulse rate digital data stream, a third analog to digital converter 140 for converting the temperature analog output to a temperature digital data stream, a fourth analog to digital converter 142 for converting the $\%O_2$ analog output to a $\%O_2$ digital data stream, and a fifth analog to digital converter 144 for converting the sound waves from the first audio amp 132 to a sound digital data stream.

The interface unit 16 further includes a multiplexer 146 for combining the digital data streams from the analog to digital converters 136–144 to a combined digital data stream. The combined digital data stream can then be conveyed to the PC 20 (FIG. 1) via a first port 148 (FIG. 6), or to the command center 18 (FIG. 1) by satellite connection B via a modem, or by radio wave connection C via the first port 148, or to the command center 18 by telephone wire, or fiber A, via telephone modem 150 (FIG. 6) and a second port 152. The digital data streams from the interface unit 16 are then converted or interpreted into readable diagnostic information in the command center 18 (FIG. 1) or the PC 20. This circuitry enables the glove members 12a and 12b and the interface unit 16 to be provided at a reasonable cost. The multiplexer 146 (FIG. 6) also communicates with a control panel and indicator circuit board 154.

The interface unit 16 further includes a speaker/microphone 156 (FIG. 6) which communicates with the multiplexer 146, via a second audio amp 158 and a sixth analog to digital converter 160, to enable a medical professional in the command center 18 (FIG. 1) to communicate orally with the persons in relative close proximity to the speaker/microphone 156 (FIG. 6).

The interface unit 16 includes a third port 164 for receiving and transmitting EKG currents detected by sensors 56a–56k to an EKG readout apparatus 22a (FIG. 1) where the EKG currents will be converted or interpreted into readable diagnostic information. The interface unit 16 (FIG. 6) further includes a fourth, fifth and sixth port 166, 168 and 170, respectively, for receiving and transmitting the analog outputs from the blood pressure circuit board 122, the temperature circuit board 124 and the $\%O_2$ circuit board 126, respectively, to a blood pressure and pulse readout apparatus 22b (FIG. 1), a temperature readout apparatus 22c, and a $\%O_2$ readout apparatus 22d, respectively, where the analog outputs will be converted or interpreted into readable diagnostic information.

The interface unit 16 (FIG. 6) also includes a power supply 172 which supplies power, via power supply distributor 174, to all of the components of the interface unit. The interface unit 16 also preferably includes a plurality battery packs 176 and a battery charger port 178.

The interface unit 16 further includes an optical isolator 180 for electrically isolating the entire interface unit 16 and glove members 12a and 12b from any destructive and damaging currents which might be encountered from external communication links.

The manner of operation of the system 10 (FIG. 1) will now be described. A person, other than the patient, places the glove probes 12a and 12b over his or her right and left hands, respectively, so that each of the person's fingers are received within a respective one of the phalange portions 32a–40a and 32b–40b, respectively. The glove members 12a and 12b are then connected to interface unit 16 by cables 14a and 14b, respectively.

EKG Diagnostic Information

To obtain EKG diagnostic information, the palmar sides 42a and 42b a of the glove members 12a and 12b are placed over the patient. The sensors 56a–56g are located at strategic positions on the glove members 12a and 12b, as described above, to enable a plurality of leadwire combinations to detect a plurality of standard leads when the glove members 12a and 12b are placed over the patient. Some exemplary leadwire combinations are as follows:

I. Single Lead Three-Leadwire Scenarios:

It is believed that at least the following ECG Leads are possible:

Lead 1:
  Positive leadwire: Sensor 56c on the tip portion of the index finger phalange portion 34a of the first glove member 12a is positioned above the patient's left breast at the left shoulder quadrant.
  Negative leadwire: Sensor 56e on the tip portion of the thumb phalange portion 32a of the first glove member 12a is positioned above and into the patient's right shoulder quadrant.
  Ground leadwire: Sensor 56a on the tip portion of the pinky finger phalange portion 40a of the first glove member 12a is positioned under the patient's left breast.

Lead 2:
  Positive leadwire: Sensor 56a on the tip portion of the pinky finger phalange portion 40a of the first glove member 12a is positioned under the patient's left breast towards the V6 position.
  Negative leadwire: Sensor 56e on the top portion of the thumb phalange portion 32a of the first glove member 12a is positioned above and into the patient's right shoulder quadrant.
  Ground leadwire: Sensor 56a on the tip portion of the pinky finger phalange portion 40a of the first glove member 12a is positioned under the patient's left breast.

Lead 3:
  Positive leadwire: Sensor 56a on the tip portion of the pinky finger phalange portion 40a of the first glove member 12a is positioned under the patient's left breast towards the V6 position.
  Negative leadwire: Sensor 56c on the tip portion of the index finger phalange portion 34a of the first glove member 12a is positioned above the patient's left breast at the left shoulder quadrant.
  Ground leadwire: Sensor 56a on the tip portion of the pinky finger phalange portion 40a of the first glove member 12a is positioned under the patient's left breast.

MCL1 (Modified Chest Lead) Lead:
  Negative leadwire: Sensor 56c on the tip portion of the index finger phalange portion 34a of the first glove member 12a is positioned above the patient's left breast at the left shoulder quadrant.
  Positive leadwire: Sensor 56g on the left side of the palm portion 28a of the first glove member 12a is positioned at the patient's right sternal border.
  Ground leadwire: Sensor 56a on the tip portion of the pinky finger phalange portion 40a of the first glove member 12a is positioned under the patient's left breast.

MCL4 Lead:
  Negative leadwire: Sensor 56c on the tip portion of the index finger phalange 34a of the first glove member 12a is positioned above the patient's left breast at the left shoulder quadrant.
  Positive leadwire: Sensor 56a on the tip portion of the pinky finger phalange portion 40a of the first glove member 12a is positioned at the patient's V4 position.
  Ground leadwire: Sensor 56a on the tip portion of the pinky finger phalange portion 40a of the first glove member 12a is positioned under the patient's left breast.

II. Five-Leadwire Scenario:

With the glove member 12a placed over the patient's left breast and the second glove member 12b placed over the patient's right wrist, it is believed that at least the following leadwires are possible:
  LL acting leadwire: Sensor 56a on the tip portion of the pinky finger phalange portion 40a of the first glove member 12a is positioned under the patient's left breast.
  RL leadwire: Sensor 56i on the tip portion of the middle finger phalange portion 36b of the second glove member 12b is positioned on the patient's right wrist.
  LA acting lead: Sensor 56c on the tip portion of the index finger phalange portion 34a of the first glove member 12a is positioned above the patient's left breast at the left shoulder quadrant.
  RA acting leadwire: Sensor 56e on the tip portion of the thumb phalange portion 32a of the first glove member 12a is positioned above and into the patient's right shoulder quadrant.
  C leadwire: Sensor 56g on the left side of the palm portion 28a of the first glove member 12a is positioned at the patient's right sternal border.

With the glove members 12a and 12b positioned in the five leadwire scenario, it is believed that the following lead readings are possible: Lead 1, Lead 2, Lead 3, AVR and AVL.

III. Seven-Leadwire Scenario:

With the glove member 12a placed over the patient's left breast and the second glove member 12b placed over the patient's right wrist, it is believed that at least the following leadwires are possible:
  LL acting leadwire: Sensor 56a on the tip portion of the pinky finger phalange portion 40a of the first glove member 12a is positioned under the patient's left breast.
  V2 leadwire: Sensor 56f on the base portion of the pinky finger phalange portion 40a of the first glove member 12a is positioned in the patient's V2 position.
  RL leadwire: Sensor 56i on the tip portion of the middle finger phalange portion 36b of the second glove member 12b is positioned on the patient's right wrist.
  V4r leadwire: Sensor 56k on the tip portion of the pinky finger phalange portion 40b of the second glove member 12b is positioned in the patient's V4r position.
  LA acting leadwire: Sensor 56c on the tip portion of the index finger phalange portion 34a of the first glove member 12a is positioned above the patient's left breast at the left shoulder quadrant.
  RA acting leadwire: Sensor 56e on the tip portion of the thumb phalange portion 32a of the first glove member 12a is positioned above and into the patient's right shoulder quadrant.
  C leadwire: Sensor 56g on the left side of the palm portion 28a of the first glove member 12a is positioned at the patient's right sternal border.

With the glove members 12a and 12b positioned in the seven leadwire scenario, it is believed that at least the following lead readings are possible: Lead 1, Lead 2, Lead 3, AVR, AVL, V2 and V4r.

IV. Modified Leadwire Scenarios.

Other EKG leadwire scenarios can be accomplished at the discretion of the command center and the person wearing the glove members 12a and 12b. Such options are available since the following glove member positions relate to electrical heart activity as below:

G (ground) leadwire: patient's left side
+ (positive) leadwire: patient's right chest (right sternal border)
− (negative) leadwire: patient's left shoulder It will be noted that the above relationships form a triangle. This triangle can be compressed or expanded, but always have the same relationships.

It should be noted that the glove members 12a and 12b of the present invention allow for a flexibility in EKG electrode positioning which has not been possible until now. With the glove members 12a and 12b positioned at the right and left shoulders, it is possible to slide a sensor 56i on the middle finger phalange portion 36b of the second glove member 12b across the patient's chest from V1 to V6 position to generate the V1–V6 leads as well as the points between the V1–V6 precordial leads. This enables one to see how the precordial electrical field changes and to determine with more accuracy the specific area of patient's heart where a possible abnormality may occur.

It should also be noted that, in the event that distortion of the EKG waveform occurs due to misplacement of the EKG sensors 56a–56k, correction of such can be accomplished using waveform modification circuits located at the command center 18. Such waveform modification circuitry accomplishes distortion correction utilizing waveshaping techniques which filter, compare, and re-shape into readable data.

V. Six-Leadwire Scenario

With the first glove member 12a placed over the patient's left breast and the second glove member 12b placed over the patient's right breast, it is believed that at least the following leadwires are possible:

6 Leadwire with Vr positions:
Positive Leadwire: Sensor 56c on the tip portion of the index finger phalange portion 34a of the first glove member 12a is positioned above the patient's left breast at the left shoulder quadrant.
Negative Leadwire: Sensor 56e on the tip portion of the thumb phalange portion 32a of the first glove member 12a is positioned above and into the patient's right shoulder quadrant.
V3r Leadwire: Sensor 56i on the middle finger phalange portion 36b of the second glove member 12b is positioned at the patient's right chest V3r position.
V4r Leadwire: Sensor 56j on the ring finger phalange portion 38b of the second glove member 12b is positioned at the patient's right chest V4r position.
V5r Leadwire: Sensor 56k on the pinky finger phalange portion 40b of the second glove member 12b is positioned at the patient's right chest V5r position.

A six leadwire scenario is especially useful in emergency settings to quickly evaluate risks in patients with acute inferior myocardial infraction.

With the glove members 12a and 12b positioned in the six leadwire scenario, it is believed that at least the following lead reading are possible: Lead 1, Lead 2, Lead 3, V4r, V5r and V6r. The above lead readings are important in diagnosing heart conditions in children, and especially infants.

As detailed above, the plurality of EKG sensors 56a–56g, being located together on two easily and quickly manipulatable glove members 12a and 12b, allows for a variety of EKG leads to be quickly and easily attained by manipulating the glove members 12a and 12b and the phalange portions 32a–40a and 32b–40b.

The EKG currents, or leads, detected from the sensors 56a–56k are transmitted to the first and second female connection plugs 64a and 64b, and through the cables 14a and 14b to the interface unit 16 where they can be sent to the command center 18 or PC 20 in a digital data stream, or to the EKG readout apparatus 22a, as discussed above.

Blood Pressure and Pulse Rate Diagnostic Information

To obtain blood pressure and pulse rate diagnostic information, the thumb phalange portion 32a (FIG. 2) and the index finger phalange portion 34a of the first glove member 12a is wrapped around one of the patient's wrist. In this position, the air bladder 72 is ready to accept air pressure from the pump 130 (FIG. 6) in the blood pressure circuit board 122. The air pump 130 then transmits inflation fluid, such as air, via the conduit 131, cable 14a and air tube 76 (FIG. 2), to the air bladder 72 to inflate the air bladder. Inflation of the air bladder 72 obliterates the radial artery. As the air bladder 72 releases the inflation fluid, pulse sound waves are acoustically picked-up by the acoustical coupler 74 and are sent over the air tube 76 to the first female connection plug 64a, and through the first cable 14a to the interface unit 16 (FIG. 1) where they can be sent to the command center 18 or PC 20 in a digital data stream, or to the blood pressure and pulse rate readout 22b, as discussed above.

Body Temperature Diagnostic Information

To obtain body temperature diagnostic information, the middle finger phalange portion 36a (FIG. 2) of the first glove member 12a is placed under the patient's tongue, or in a suitable orifice, for a period of time sufficient to receive temperature signals from the thermistor 78, preferably about one minute. The temperature signals from the temperature device 48 can be transmitted to the first female connection plug 64a, and through the first cable 14a to the interface unit 16 (FIG. 1) where they can be sent to the command center 18 or PC 20 in a digital data stream, or to the temperature readout apparatus 22d, as discussed above.

%$O_2$ Diagnostic Information

To obtain %$O_2$ diagnostic information, the thumb phalange portion 32b (FIG. 3) and the index finger phalange portion 34b of the second glove member 12b are pressed against one of the patient's finger tips. In this position, the red LED emitter 82 (FIG. 4) emits red and infra-red light toward the LED sensor 84. When the light from the LED emitter 84 is passed through the patient's finger (non-painted finger nails only) at the finger nail, the LED sensor 84 detects the color light waves present. These signals are translated from light intensity and color quality to oxygen levels. More oxygen yields a light red blood while less oxygen produces a darker red to purple blood. It should be noted that pulse rate can also be ascertained from these readings. As an alternative to the finger tips, the ear lobes could be used to measure the %$O_2$.

The %$O_2$ signals from the %$O_2$ device 50 are then sent to the second female connection plug 64b, and through the second cable 14b to the interface unit 16 (FIG. 1) where the %$O_2$ signals can be sent to the command center 18 or PC 20 in a digital data stream, or to the %$O_2$ readout apparatus 22c, as discussed above.

Auscultation Diagnostic Information

To listen to the heart and lungs of the patient, the first glove member 12a is moved over the patient's body to enable the acoustical coupler and microphone 90 to pick up, or hear, sound waves from the patient's heart and lungs, much like a stethoscope would. The sound waves are then transmitted to the first female connection plug 64a, via the pair of wires 93, and then through the first cable 14a to the interface unit 16, where they can be sent to the command center 18 or PC 20, in a digital data stream as described above. Alternatively, the sound waves from the acoustical coupler of the acoustical coupler and microphone 90 could also be conducted via air tube 94 to a stethoscope 22e.

Oral Communication

To communicate orally with a remote location, such as the command center 18, the speaker/microphone 156 can transmit and receive sound waves as described above. It should be noted that the interface unit 16 may not be able to transmit or receive sound waves via the speaker/microphone 156 when processing diagnostic information from the EKG diagnostic device, the blood pressure device 46, the temperature device 48, the %$O_2$ device 50 and/or the auscultation device 52. The ability for a doctor to communicate with the patient, if alert, and people proximate to the patient, such as the person manipulating the glove members 12a and 12b, if such person is not the doctor, allows the doctor to instruct the person manipulating the glove members 12a and 12b to best obtain the diagnostic information and to instruct the person manipulating the glove members, or other near by the patient how to provide care/treatment to the patient.

Defibrillator Device

Once the diagnostic information from any, or all, of the EKG device, the blood pressure device 46, the temperature device 48, the %$O_2$ device 50, the auscultation device 52, and the oral information obtained via the speaker/microphone 156 has been received by a doctor in the command center 18 or accessible to the PC 20 or the readout apparatus 22a–22e, the doctor can decide on the best way to treat the patient. If the information obtained by the doctor indicates that the patient is in ventricular fibrillation (i.e., the heart beats in an uneven and inefficient fashion, virtually stopping the heart's ability to pump blood), the doctor instructs the person manipulating the glove to defibrillate the patient. Of course, if the doctor is with the patient and is manipulating the glove members 12a and 12b herself, then the doctor would defibrillate the patient herself.

To defibrillate the patient, the dorsal sides 44a and 44b of the first and second glove members 12a and 12b, respectively, are positioned on the patient's chest area so that the electrodes 98a–h contact the patient's chest area. The acupuncture/defibrillator circuit board 128 (FIG. 6) is activated to ready the high voltage source 134 to deliver a powerful electrical shock to the patient's heart. The high voltage source 134 delivers power, preferably about 130–300 Joules per shock, through the cables 14a and 14b to the electrodes 98a–k on the first and second glove members 12a and 12b to deliver the electric shock to the patient's heart to bring the patient out of ventricular fibrillation. The acupuncture/defibrillator circuit board 128 can be activated either by the command center 18 or by a person near the interface unit 16. In the event that the acupuncture/defibrillator circuit board 128 is to be activated by a person near the interface unit, such as the person manipulating the glove members, the delivery of power can be delayed for a period of time, preferably about five seconds, after activation of the circuit board 128 to enable proper placement of the electrodes 98a–h.

The delivery of electrical shock to the patient's heart can be repeated as necessary to bring the patient out of ventricular fibrillation to restore the patient's heartbeat to an even and efficient fashion (i.e., a regular rhythm). The glove members 12a and 12b, having both an EKG device and a defibrillator device, enables the person manipulating the glove members to quickly and easily alternate between taking EKG readings, to monitor the condition of the patient's heart, and the defibrillator device with only a quick rotation of their hands.

Once the patient's heartbeat has been restored to a regular rhythm, the next step is to maintain the patient's heart in a regular rhythm. To do so, a first aid kit is preferably provided with the interface unit 16. The first aid kit would preferably include medications which would include an anti-arrythmic drug, such as Lidocaine, for inhibiting the heart from falling back into ventricular fibrillation, a lactic acidosis neutralizer, such as sodium bicarbonate and pain relieving medications like demerol or morphine. These medications would preferably be preloaded in clearly marked and color coded syringes to enable quick administration. If the doctor were not near the patient and is operating out of the command center 18, the doctor can monitor the patient's condition via the glove members 12a and 12b and the interface unit 16 and can instruct the person manipulating the glove members 12a and 12b and/or persons near the patient to properly provide care/treatment for the patient.

Acupuncture Device

To provide electrical pin stimulations, the acupuncture/defibrillator circuit board 128 is activated to cause the high voltage source 134 to deliver power to the electrodes 106a–106j. The high voltage source 134 delivers power, preferably about 5 to 10 Joules per electrode 106a–106j, through the cables 14a and 14b to the electrodes 106a–106j on the first and second glove members 12a and 12b to enable the electrodes 106a–106j to provide electrical pin stimulation to the patient when the electrodes 106a–106j are moved over the patient's body.

The electrical pin stimulation from the electrodes 106a–106j can be used to alleviate pain, as is done via conventional acupuncture practice, albeit in a non-invasive manner. This glove mediated acupuncture technique obviates the need to insert needles into the body to deliver acupuncture and helps insure safety from needle transmitted diseases, such as HIV infection. The electrical pin stimulations can also be used to cauterize wounds on the patient.

Accordingly, the above-described present invention enables a plurality of diagnostic information to be quickly and accurately obtained, either by a doctor in close proximity to a patient, or by a doctor remote from the patient (i.e., when the doctor is in the command center 18), evaluate and/or monitor a patient's condition. The present invention also provides a means for quickly treating a patient (i.e., the defibrillator device 54 and the acupuncture device) under the care of a doctor who is accurately informed of the patient's condition even when the doctor is not near the patient.

While the best modes for carrying out the invention have been described in detail, those familiar with the art to which the invention relates will appreciate other ways of carrying out the invention defined by the following claims. For instance, the placement of the diagnostic devices on the glove members 12a and 12b and/or specific design of the diagnostic devices could vary from that described above. For instance, the EKG device could have more or fewer sensors or the sensors could be located differently than that described above.

What is claimed is:

1. A system for collecting a plurality of diagnostic information and transmitting the diagnostic information to a remote location and for providing emergency treatment, said system comprising:

a first member contoured to at least a portion of a person's first hand and a second member contoured to at least a portion of a person's second hand, said members comprising a plurality of diagnostic devices and a defibrillator device, said diagnostic devices capable of sensing diagnostic signals from a person; and a transmitting unit for transmitting information to, and receiving information from, a remote location.

2. The system of claim 1 wherein said plurality of diagnostic devices includes an EKG diagnostic device, a blood pressure and pulse diagnostic device and a temperature device.

3. The system of claim 2 wherein said plurality of diagnostic devices further includes a %O$_2$ diagnostic device and an auscultation device.

4. The system of claim 3 wherein said members further include an acupuncture device having a plurality of electrodes located on said members.

5. The system of claim 2 wherein said diagnostic devices are capable of sensing diagnostic signals when the members are worn on a persons hand.

6. The system of claim 1 further including a first aid kit comprising Lidocaine.

7. The system of claim 1 wherein said members have a shape that corresponds to at least a substantial portion of a person's hand such that each of said members is capable of being worn on a person's hand.

8. The system of claim 7 further comprising a satellite modem, wherein the remote location comprises a command center and said interface units transmits information to, and receives information from, the remote location via a satellite connection through said satellite modem.

9. The system of claim 7 further comprising a telephone modem, wherein the remote location comprises a command center and said interface units transmits information to, and receives information from, the remote location via a telephone wire connection through said telephone modem.

10. The system of claim 7 wherein said members, when worn on the hands, cover at least about a majority of the hands.

11. A diagnostic probe comprising:

a first and second glove member, each of said glove members comprising a palm portion, a wrist portion and a plurality of phalange portions, each of said glove members adaptable to be worn on one of a person's hand;

an EKG diagnostic device located on said glove members;

a blood pressure and pulse rate device located on one of said glove members;

a temperature device located on one of said glove member; and a defibrillator device located on said glove members.

12. The diagnostic probe of claim 11 further comprising a %O$_2$ device located on one of said glove members and an auscultation device located on one of said glove members.

13. The diagnostic probe of claim 12 further comprising an acupuncture device located on said glove members.

14. The system of claim 11 wherein said blood pressure and pulse rate device is located on at least two of said phalange portions of one of said member and includes an inflatable air bladder.

15. The system of claim 11 wherein said EKG diagnostic device includes at least a first EKG sensor located on said palm portion of said first member, and a second EKG sensor located on at least one of said phalange portions of said first member.

16. The system of claim 15 wherein said EKG diagnostic device includes at least seven EKG sensors.

17. A system for collecting a plurality of diagnostic information and transmitting the diagnostic information to a remote location and for providing emergency treatment, said system comprising;

a first member adaptable to be worn on a person's first hand and a second member adaptable to be worn on a person's second hand, said members comprising a plurality of diagnostic devices and a defibrillator device, said diagnostic devices capable of sensing diagnostic signals from a person, each of said first and second members comprising a palm portion, a wrist portion and five phalange portions; and a transmitting unit for transmitting information to, and receiving information from, a remote location.

18. The system of claim 14 wherein said temperature device includes a thermistor which is responsive to temperature changes.

19. The system of claim 18 wherein said %O$_2$ device includes a LED emitter and an LED sensor, said led sensor and led emitter being located on one of said phalange portions.

20. The system of claim 19 wherein said interface unit comprises an EKG circuit board, a blood pressure and pulse rate circuit board, a temperature board, a %O$_2$ circuit board, wherein said blood pressure and pulse rate circuit board includes a source of inflation fluid for inflating said air bladder.

21. The system of claim 20 wherein said interface unit includes at least one analog to digital converter for converting at least one analog output from at least one of said circuit boards to a digital data stream.

22. The system of claim 17 wherein said defibrillator device includes a plurality of electrodes being located on said members.

23. A system for collecting diagnostic information and transmitting the diagnostic information to a remote location and for providing emergency treatment, said system comprising:

a first member contoured to at least a portion of a first person's first hand and a second member contoured to at least a portion of the first person's second hand, said members having at least one diagnostic device capable of sensing diagnostic signals from a second person, said members further comprising a defibrillator device; and a transmitting unit for transmitting information to, and receiving information from, a remote location.

24. The system of claim 23 wherein each of said members comprise a glove.

25. The system of claim 24 wherein said member comprises a palm portion, a wrist portion and five phalange portions.

26. The system of claim 23 wherein said members have a shape that corresponds to at least a substantial portion of a person's hand such that each of said members is capable of being worn on a person's hand.

27. The system of claim 26 wherein said members have a portion shaped to contour to a person's palm.

28. The system of claim 26 wherein said members have a portion shaped to contour to a person's finger.

29. The system of claim 28 wherein said members have a portion shaped to contour to a person's palm.

30. The system of claim 26 wherein said members comprise a wrist portion and a palm portion.

31. The system of claim 26 wherein said members comprise a palm portion and a phalange portion.

32. The system of claim 26 wherein said members have a palmar side, each of said members having at least one sensor on said palmar side of said member.

33. The system of claim 32 wherein said members have a dorsal side.

34. The system of claim 32 further comprising an electrical connection plug capable of communicating with said device and said interface unit, said members further comprising electrical circuitry providing electrical communication between said device and said plug.

35. The system of claim 26 wherein the information that said interface unit is capable of receiving comprises sound waves.

36. The system of claim 26 wherein said interface unit comprises a speaker.

37. The system of claim 36 wherein said interface unit comprises a microphone.

38. The system of claim 26 wherein each of said members has a palmar side, said diagnostic device comprising at least one sensor located on said palmar side of one of said members.

39. The system of claim 38 wherein each of said members has a dorsal side, said defibrillator device comprising a plurality of defibrillator electrodes, at least one of the defibrillator electrodes being located on said dorsal side of said first member.

40. The system of claim 38 wherein said diagnostic device comprises an EKG diagnostic device and said sensor comprises a first EKG sensor.

41. The system of claim 40 wherein each of said member comprise a palm portion.

42. The system of claim 41 wherein said sensor is located on said palm portion of said first member.

43. The system of claim 41 wherein said first member further comprises five phalange portions, said sensor being located on one of said phalange portions of said first member.

44. The system of claim 40 wherein said EKG diagnostic device includes at least seven EKG sensors.

45. The system of claim 40 wherein said EKG device comprises a plurality of EKG sensors.

46. The system of claim 26 wherein said members comprise a plurality of diagnostic devices.

47. The system of claim 46 wherein said plurality of diagnostic devices includes an EKG diagnostic device, a blood pressure and pulse diagnostic device and a temperature device.

48. The system of claim 47 wherein said plurality of diagnostic devices further includes a %$O_2$ diagnostic device and an auscultation device.

49. The system of claim 48 wherein said members further include an acupuncture device having a plurality of electrodes located on said members.

50. The system of claim 47 wherein each of said first and second members comprise a palm portion, a wrist portion and five phalange portions.

51. The system of claim 50 wherein said blood pressure and pulse rate device is located on at least two of said phalange portions of one of said member and includes an inflatable air bladder.

52. The system of claim 46 wherein said plurality of diagnostic device comprises at least two diagnostic devices selected from the group consisting of an EKG device, a blood pressure and pulse rate device, a temperature device, a percent $O_2$ device, and an auscultation device.

53. The system of claim 46 wherein said plurality of diagnostic device comprises at least three diagnostic devices selected from the group consisting of an EKG device, a blood pressure and pulse rate device, a temperature device, a percent $O_2$ device, and an auscultation device.

54. The system of claim 46 wherein said plurality of diagnostic device comprises at least four diagnostic devices selected from the group consisting of an EKG device, a blood pressure and pulse rate device, a temperature device, a percent $O_2$ device, and an auscultation device.

55. The system of claim 26 wherein said plurality of diagnostic device comprises EKG device, a blood pressure and pulse rate device, a temperature device, a percent $O_2$ device, and an auscultation device.

56. The system of claim 26 wherein said diagnostic device is selected from the group consisting of an EKG device, a blood pressure and pulse rate device, a temperature device, a percent $O_2$ device, and an auscultation device.

57. The system of claim 26 wherein said defibrillator device comprises a plurality of defibrillator electrodes.

58. The system of claim 57 wherein each of said members have a dorsal side, at least one of the defibrillator electrodes being located on said dorsal of said first member.

59. A diagnostic probe comprising:
   a member contoured to at least a portion of a first person's hand, said member having a palmar side;
   at least one diagnostic device having at least one sensor capable of sensing diagnostic signals from a second person on said palmar side of said member; and
   at least one defibrillator electrode on said member.

60. The probe of claim 59 wherein said at least one diagnostic device comprises a plurality of diagnostic devices.

61. The probe of claim 60 wherein said plurality of diagnostic devices includes an EKG diagnostic device, a blood pressure and pulse diagnostic device and a temperature device.

62. The probe of claim 59 wherein said member comprises a palm portion, a wrist portion and five phalange portions.

63. The probe of claim 62 wherein said member comprises a glove.

64. The probe of claim 59 wherein said member has a shape that corresponds to at least a substantial portion of a person's hand such that said member is capable of being worn on a person's hand.

65. The probe of claim 64 wherein said member has a dorsal side.

66. The probe of claim 64 wherein said at least one diagnostic device comprises a plurality of diagnostic devices.

67. The probe of claim 66 wherein said plurality of diagnostic devices includes an EKG diagnostic device, a blood pressure and pulse device and a temperature device.

68. The probe of claim 66 wherein said plurality of diagnostic device comprises at least two diagnostic devices selected from the group consisting of an EKG device, a blood pressure and pulse rate device, a temperature device, a percent $O_2$ device, and an auscultation device.

69. The probe of claim 66 wherein said plurality of diagnostic device comprises at least three diagnostic devices selected from the group consisting of an EKG device, a blood pressure and pulse rate device, a temperature device, a percent $O_2$ device, and an auscultation device.

70. The probe of claim 66 wherein said plurality of diagnostic device comprises at least four diagnostic devices selected from the group consisting of an EKG device, a blood pressure and pulse rate device, a temperature device, a percent $O_2$ device, and an auscultation device.

71. The probe of claim 66 wherein said plurality of diagnostic device comprises EKG device, a blood pressure and pulse rate device, a temperature device, a percent $O_2$ device, and an auscultation device.

72. The probe of claim 66 further comprising an electrical connection plug capable of communicating with said devices and an information transmission device, said probe further comprising electrical circuitry providing electrical communication between said devices and said plug.

73. The probe of claim 64 further comprising electrical circuitry for providing communication between said diagnostic device and an information transmission device.

74. The probe of claim 64 wherein said member has a portion shaped to contour to a person's palm.

75. The probe of claim 64 wherein said member has a portion shaped to contour to a person's finger.

76. The probe of claim 75 wherein said member has a portion shaped to contour to a person's palm.

77. The probe of claim 64 wherein said member comprises a wrist portion and a palm portion.

78. The probe of claim 64 wherein said member comprises a palm portion and at least one phalange portion.

79. The probe of claim 64 wherein said diagnostic device comprises an EKG diagnostic device comprising a plurality of EKG sensors.

80. The probe of claim 79 wherein said member comprises a palm portion, a wrist portion and at least one phalange portion, wherein said EKG sensor are located on at least one of said palm portion, said wrist portion, and said phalange portion.

81. The probe of claim 80 wherein said EKG sensors are located on said member on at least two of said palm portion, said wrist portion, and said phalange portion.

82. The probe of claim 81 wherein said EKG sensors are located on said member on said palm portion, said wrist portion and said phalange portion.

83. The probe of claim 64 wherein said at least one defibrillator electrode comprises a plurality of defibrillator electrodes.

84. The probe of claim 83 wherein said member comprises a dorsal side, said defibrillator electrodes being located on said dorsal side of said member.

85. The probe of claim 64 said diagnostic device comprises an EKG diagnostic device and said sensor comprises a first EKG sensor.

86. The probe of claim 64 wherein said diagnostic device is selected from the group consisting of an EKG device, a blood pressure and pulse rate device, a temperature device, a percent $O_2$ device, and an auscultation device.

87. The probe of claim 64 wherein said at least one defibrillator electrode comprises a plurality of defibrillator electrodes.

88. The probe of claim 87 wherein said member has a dorsal side, said defibrillator electrodes being located on said dorsal side of said member.

89. A system for collecting diagnostic information and transmitting the diagnostic information to a remote location and for providing emergency treatment, said system comprising:
a first member contoured to at least a portion of a first person's first hand and a second member contoured to at least a portion of the first person's second hand, said members having at least one diagnostic device capable of sensing diagnostic signals from a second person; and
a transmitting unit for transmitting information to, and receiving information from, a remote location.

90. The system of claim 89 wherein said members have a shape that corresponds to at least a substantial portion of a person's hand such that each of said members is capable of being worn on a person's hand.

91. The system of claim 90 wherein each of said members has a palmar side, said diagnostic device comprising at least one sensor located on said palmar side of one of said members.

92. The system of claim 91 wherein each of said members has a dorsal side, said system further comprising a defibrillator device comprising a plurality of defibrillator electrodes, at least one of the defibrillator electrodes being located on said dorsal side of said first member.

93. The system of claim 91 wherein said diagnostic device comprises an EKG diagnostic device and said sensor comprises a first EKG sensor.

94. The system of claim 93 wherein each of said members comprise a glove.

95. The system of claim 94 wherein said at least one diagnostic device comprises a plurality of diagnostic devices.

96. The system of claim 95 wherein said plurality of diagnostic device comprises at least two diagnostic devices selected from the group consisting of an EKG device, a blood pressure and pulse rate device, a temperature device, a percent $O_2$ device, and an auscultation device.

97. The system of claim 95 wherein said plurality of diagnostic device comprises at least three diagnostic devices selected from the group consisting of an EKG device, a blood pressure and pulse rate device, a temperature device, a percent $O_2$ device, and an auscultation device.

98. The system of claim 95 wherein said plurality of diagnostic device comprises at least four diagnostic devices selected from the group consisting of an EKG device, a blood pressure and pulse rate device, a temperature device, a percent $O_2$ device, and an auscultation device.

99. The system of claim 95 wherein said plurality of diagnostic device comprises EKG device, a blood pressure and pulse rate device, a temperature device, a percent $O_2$ device, and an auscultation device.

100. The system of claim 90 wherein said diagnostic device is selected from the group consisting of an EKG device, a blood pressure and pulse rate device, a temperature device, a percent $O_2$ device, and an auscultation device.

* * * * *

UNITED STATES PATENT AND TRADEMARK OFFICE
CERTIFICATE OF CORRECTION

PATENT NO.      : 6,248,064 B1
DATED           : June 19, 2001
INVENTOR(S)     : Govindan Gopinathan and Arthur R. Tilford It is certified that error appears in the above-identified patent and that said Letters Patent is hereby corrected as shown below:

Column 18,
Lines 1 and 5, delete "11" and replace with -- 17 --.
Lines 30 and 31, delete "led" and replace with -- LED --.

Column 20,
Line 4, delete "device" and replace with -- devices --.
Line 17, delete "26" and replace with -- 46 --.

Column 22,
Lines 37, 42, 47 and 52, delete "device" and replace with -- devices --.

Signed and Sealed this

Thirteenth Day of April, 2004

JON W. DUDAS
*Acting Director of the United States Patent and Trademark Office*